United States Patent [19]

Wong

[11] Patent Number: 4,994,548
[45] Date of Patent: Feb. 19, 1991

[54] MODIFIED BISPHENOL RESINS HAVING AT LEAST ONE ARYLCYCLO-BUTANENEALKYL MOIETY

[75] Inventor: Pui K. Wong, Katy, Tex.

[73] Assignee: Shell Oil Company, Houston, Tex.

[21] Appl. No.: 509,839

[22] Filed: Apr. 17, 1990

Related U.S. Application Data

[63] Continuation-in-part of Ser. No. 349,544, May 9, 1989, Pat. No. 4,960,956.

[51] Int. Cl.$^5$ .............................................. C08G 65/38
[52] U.S. Cl. ...................................... 528/219; 528/86; 568/722
[58] Field of Search ................... 528/86, 219; 568/722

[56] References Cited

U.S. PATENT DOCUMENTS 4,540,763  9/1985  Kirchhoff ............................ 526/281
4,642,329  2/1987  Kirchhoff et al. .................. 526/284
4,822,930  4/1989  Liu ..................................... 570/206

*Primary Examiner*—Harold D. Anderson
*Assistant Examiner*—T. Mosley

[57] ABSTRACT

Rigid, relatively insoluble resins of the thermoset type are produced by heating ring-arylcyclobutenealkylated di(hydroxyphenyl) compounds having at least one arylcyclobutenealkyl moiety attached to at least one of the phenyl rings.

12 Claims, No Drawings

MODIFIED BISPHENOL RESINS HAVING AT LEAST ONE ARYLCYCLO-BUTANENEALKYL MOIETY

RELATED APPLICATIONS

This application is a continuation-in-part of copending application Ser. No. 349,544 filed May 9, 1989 now U.S. Pat. No. 4,609,956 (10-2-90).

1. Field of the Invention

This invention relates to cured products derived from certain ring-alkylated derivatives of di(hydroxyphenyl) compounds. More particularly, the invention relates to cured products obtained by heating di(hydroxyphenyl) compounds having at least one arylcyclobutenealkyl moiety attached to at least one of the phenyl rings.

2. Background of the Invention

The curing of monomeric materials to produce polymeric thermoset resins is well known in the art. In general, the curable monomers have one and customarily more than one active group which serves as a reactive site for the curing or crosslinking polymerization to produce a crosslinked polymer. However, for efficient curing of many or most polymerizable monomers to produce crosslinked resins, for example the curing of an epoxy resin, the presence of a curing agent, catalytic or stoichimetric, is required to cause the curing or crosslinking to occur at an acceptable rate. Even in the presence of most curing agents the rate of curing is undesirably slow and the addition of an accelerator is required to obtain sufficiently rapid curing. Certain polymerizable monomers do cure in the absence of added curing agent or accelerator but only upon the application of high intensity energy, e.g., ultraviolet (UV) light.

There are, however, other monomeric materials which contain one or more active sites such that curing will take place upon application of heat. One class of such crosslinked resin precursor includes within the molecular structure one or more moieties of an arylcyclobutene, particularly a benzocyclobutene. Without wishing to be bound by any particular theory, it appears likely that upon application of heat the cyclobutene moieties undergo ring-opening to produce reactive intermediates which react with active portions of adjacent molecules. The resulting resin have properties of rigidity and resistance to many common solvents.

A series of U.S. patents to Kirchhoff, of which U.S. Pat. No. 4,540,763 is illustrative, describes the production and curing of a large number of benzocyclobutene derivatives including multi-cyclic aromatic compounds in which the aromatic rings are directly connected, or connected by a functional group, to a carbon atom of the six-membered ring of a benzocyclobutene moiety. These derivatives are said to be self-curing. It would be of advantage, however, to provide a novel class of self-curing benzocyclobutene-type compounds of a different molecular structure.

SUMMARY OF THE INVENTION

This invention provides novel cured products produced from arylcyclobutene derivaties of di(hydroxyphenyl) compounds. More particularly, the invention relates to cured products obtained by subjecting arylcyclobutenealkylated di(hydroxyphenyl) compounds to the influence of heat.

DESCRIPTION OF THE INVENTION

The cured compositions of the invention are produced from di(hydroxyphenyl) compounds of up to two aromatic rings having on at least one of the aromatic rings an arylcyclobutene-containing substituent where the phenyl group of the di(hydroxyphenyl) compound is connected to a ring carbon of an aromatic 6-membered ring of an arylcyclobutene moiety by an alkylene linking group. These precursors are produced by reaction of a di(hydroxyphenyl) compound with an arylcyclobutenealkyl compound. The compositions of the invention are rigid polymers produced at elevated temperature.

The di(hydroxyphenyl) compounds which are suitably employed as precursors of the compositions of the invention have up to 30 carbon atoms and from 1 to 2 aromatic rings, inclusive. When two aromatic rings are present, the rings are fused or are connected by a direct valence bond, alkylene of up to 8 carbon atoms, inclusive, oxy, thio, carbonyl, carboxyl, carbonato or sulfonyl. One class of such di(hydroxyphenyl) compounds is represented by the formula $$HO-X-OH \qquad (I)$$

wherein X is aromatic having up to 30 carbon atoms and from 1 to 2 aromatic rings which, when two rings are present are fused or joined as described above and have at least one hydroxyl substituent on each aromatic ring. The moiety X in formula I is otherwise hydrocarbyl containing only atoms of carbon and hydrogen besides any additional atoms present in divalent linking groups or is substituted hydrocarbyl containing additional atoms present as unreactive carbon atom substituents, e.g., halogens, preferably the middle halogens chloro or bromo. Illustrative di(hydroxyphenyl) compounds of formula I include hydroquinone, resorcinol, 1,5-dihydroxynaphthalene, 4,4'-dihydroxy-2,2'-dimethylbiphenyl, 2,2-di(4-hydroxyphenyl)-propane, di(4-hydroxyphenyl)methane, 2,2-bis(4-hydroxy-3,5-dibromophenyl)-propane, di(3-hydroxyphenyl) ether, di(4-hydroxy-3-ethylphenyl) ketone or di(4-hydroxyphenyl) carbonate.

A preferred class of di(hydroxyphenyl) compounds is represented by the formula

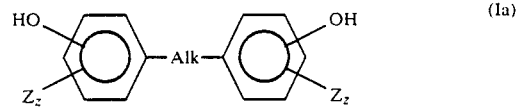

wherein Alk is alkylene of up to 8 carbon atoms, Z independently is alkyl, preferably lower alkyl of up to 4 carbon atoms inclusive, or halo, preferably middle halo, and z independently is an integer from 0 to 3 inclusive, preferably 0 to 2. These di(hydroxyphenyl) compounds are illustrated by di(3-hydroxyphenyl)methane, 1,1-di(4-hydroxy-3-methylphenyl)-ethane, 2,2-di(4-hydroxyphenyl)propane, 4,4-di(4-hydroxy-3-chlorophenyl)-octane, 2,2-bis(4-hydroxy-3,5-dibromophenyl)propane and 2-(3-hydroxyphenyl)-2-(2-hydroxyphenyl)propane. The preferred hydroxyl substitution is para to the carbon atom connected to the Alk group and z is most preferably zero. The compound 2,2-di(4-hydroxyphenyl)propane, also known as bisphenol A or BPA, is a particularly preferred di(hydroxyphenyl) compound.

The di(hydroxyphenyl) compounds are known compounds or are produced by known methods.

To produce the ring-alkylated di(hydroxyphenyl) compounds, the di(hydroxyphenyl) compounds are reacted with an arylcyclobutenealkyl compound represented by the formula $$Ar-R-W \qquad (II)$$

wherein Ar is an arylcyclobutene group, R is alkylene of up to 4 carbon atoms inclusive and W is an electron-withdrawing group.

Suitable W groups in the above formula II are those which when attached to an aromatic ring are thought to be ring-deactivating and meta-directing, or, expressed differently, are those groups commonly referred to as good "leaving groups" in nucleophillic substitution reactions. Preferred W groups are upper halo, i.e., halogens other than fluoro (chloro, bromo or iodo), or sulfonic ester such as aryl sulfate, e.g., tosylate, brosylate or nosylate, alkyl sulfonate, e.g., mesylate and fluoroalkyl sulfonate, for example triflate or nonaflate. The term R of formula II is alkylene of up to 4 carbon atoms, e.g., methylene, 1,2-ethylene or 1,4-butylene, but preferably is methylene.

The arylcyclobutene group Ar is an aromatic ring system of up to 4 aromatic rings and up to 30 carbon atoms, inclusive, which contains at least one cyclobutene ring fused to an aromatic ring. Suitable aromatic ring systems are illustrated by the single aromatic ring system compound benzene, the fused aromatic ring system compounds naphthalene, anthracene and phenanthrene, the directly joined aromatic ring system compounds of two or more aromatic rings joined by an alkylene group of up to 8 carbon atoms inclusive, e.g., diphenylalkanes such as diphenylmethane and 2,2-diphenylpropane. The preferred aromatic ring system is the single ring system compound benzene and the preferred arylcyclobutene moiety is a benzocyclobutene moiety. The Ar group is hydrocarbyl containing only atoms carbon and hydrogen or is substituted hydrocarbyl containing additional atoms as inert carbon atom substituents, e.g., cyano or middle halo. The preferred Ar group is a benzocyclobutene group.

In a particularly preferred embodiment of the invention, the arylcyclobutenealkyl compound is a halomethylcyclobutene of the formula

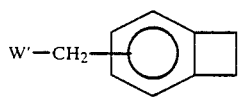
(IIa)

wherein W' is upper halo, i.e., chloro, bromo or iodo, but preferably is chloro or bromo, especially chloro. The halomethylcyclobutenes are prepared by one of several reaction schemes depending upon the desired spatial arrangement of the halomethyl substituent and the cyclobutene ring. A 4-halomethylbenzocyclobutene is prepared from p-methylbenzyl halide, preferably p-methylbenzyl chloride, in two steps according to the procedure of Ewing et al, J. Chem. Soc. Chem. Comm., 1979, 207. Preparation of 3-chloromethylbenzocyclobutene is effected by a similar procedure starting with o-methylbenzyl chloride. In this case, however, the procedure yields about 1:2 molar mixture of 3-chloromethylbenzocyclobutene and 4-chloromethylbenzocyclobutene. This mixture is separated into its individual components by conventional methods such as distillation or chromatographic separation or alternatively is used as such without separation of the isomers. Other arylcyclobutenealkyl compounds are also known compounds or are produced by known methods.

The di(hydroxyphenyl) compound and the arylcyclobutenealkyl compound are reacted in the liquid phase in the presence of what is commonly referred to as a Friedel Crafts alkylation catalyst. Such catalysts include acidic metal halides such as aluminum trichloride, boron trifluoride, zinc chloride, stannic chloride and ferric chloride, proton-containing acids such as sulfuric acid, hydrofluoric acid and phosphoric acid, acidic metal oxides such as silica and ferric oxide, and cationic exchange resins such as the class of sulfonated styrenedivinylbenzene crosslinked resins marketed under the trademarks DOWEX ™ Resin and AMBERLITE ™ Resin. The alkylation catalyst is employed in a catalytic quantity. Amounts of alkylation catalyst from about 1% to about 5% by weight, based on total reactants, are satisfactory, although higher or lower amounts may also be used. The alkylation reaction is conducted in a liquid phase in an inert reaction diluent. Suitable reaction diluents are liquid under reaction conditions and are capable of dissolving at least a portion of each reactant at reaction temperature. Illustrative of suitable reaction diluents are hydrocarbons or halohydrocarbons of up to 12 carbon atoms inclusive, including heptane, isooctane and dodecane as well as ethylene dichloride, carbon tetrachloride, perfluorobutane and perchloropropane. The preferred diluents are 1,2-dichloroethane and chloroform, especially 1,2-dichloroethane.

The alkylation reaction is conducted by contacting the di(hydroxyphenyl) compound, the arylcyclobutenealkyl compound and the catalyst in the reaction diluent and maintaining the mixture under alkylation conditions, while reactant/catalyst contact is maintained through conventional methods such as shaking, stirring or refluxing. The ratio of di(hydroxyphenyl) compound to arylcyclobutenealkyl compound is not critical although the ratio will influence the number of arylcyclobutene moieties introduced onto each di(hydroxyphenyl) compound molecule. In general, molar ratios of the di(hydroxyphenyl) compound to the arylcyclobutenealkyl compound from about 8:1 to about 1:8 are satisfactory although molar ratios from about 4:1 to about 1:1 are preferred.

Suitable reaction temperatures are from about 20° C. to about 180° C. with reaction temperatures in the range from about 30° C. to about 150° C. being preferred. Good results are often obtained at the reflux temperature of the reaction mixture under ambient temperature. The reaction pressures that are suitable are those pressures which will maintain the reaction mixture in a liquid phase at reaction temperature. Such pressures are typically up to about 20 atmospheres but more often are from about 0.8 atmospheres but more often are from about 0.8 atmosphere to about 10 atmospheres. Subsequent to reaction the ring-alkylated di(hydroxyphenyl) product is recovered by conventional methods such as diluent removal or filtration following precipitation of the product with a non-soluent.

The ring alkylated di(hydroxyphenyl) compounds which cure into the compositions of the invention are characterized by the presence as a substituent on at least one phenyl ring of the di(hydroxyphenyl) compound of a —R—Ar group wherein Ar and R have the previously stated meanings. Some of the di(hydroxyphenyl) compounds will have more than one Ar—R— group within the molecule and some many have more than one Ar—R— group on the same phenyl ring. The location and number of Ar—R— groups is not critical, although the number of such groups will in part control the degree of crosslinking which will occur when the ring-alkylated product is cured. In terms of the reactants as described above (formula I and formula II), the products are illustrated by the formula

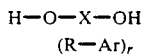
(III)

wherein Ar, R and X have the previously stated meanings and r is an integer from 1 to 4 inclusive, preferably from 1 to 2 inclusive. In terms of the preferred reactants of formulas Ia and IIa the preferred ring-alkylated products are represented by the formula

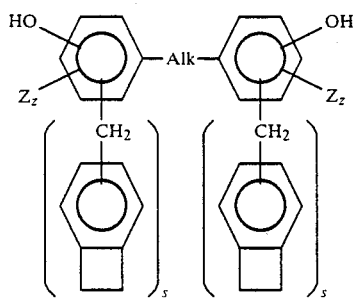
(IIIa)

wherein Alk, Z, z and Ar have the previously stated meanings and s independently is an integer from 0 to 2, preferably 0 to 1, inclusive with the proviso that at least one s is at least 1.

The nomenclature of the ring-alkylated products is somewhat difficult because of the complexity thereof, but representative products include di(4-benzocyclobutenylmethyl)-2,2-di(4-hydroxyphenyl)propane illustratively produced from 4-chloromethylbenzocyclobutene and 2,2-di(4-hydroxyphenyl)propane and tri(3-benzocyclobutenylmethyl)-1,5-dihydroxynaphthalene illustratively produced from 3-bromomethylbenzocyclobutene and 1,5-dihydroxynaphthalene. Other products will be apparent from consideration of the above formulas for the reactants and the product.

The arylcyclobutenealkylated di(hydroxyphenyl) compound products are generally viscous oils or low-melting solids, the properties of which depend in part on the number of arylcyclobutenealkyl moieties per molecule. Products having a single arylcyclobutenealkyl moiety per molecule do not extensively cure or crosslink but will provide, upon heating, a rigid, at least relatively insoluble product. Arylcyclobutenealkylated di(hydroxyphenyl) compound products having two or more alkylcyclobutenealkyl moieties will extensively cure or crosslink to provide a product more clearly of the type termed thermoset resin. In either case, the curing of the products of the invention is effected by the application of elevated temperature. Typically the products are heated to a temperature up to about 300° C. but more often to a temperature of at least about 200° C. The resulting rigid, relatively insoluble products exhibit at least some degree of self-polymerization and in some cases a considerable degree of polymerization.

Alternatively, the ring-alkylated di(hydroxyphenyl) compounds serve to crosslink polymeric materials of a variety of types including those having carbon-carbon unsaturation within the polymeric molecule such as polybutadiene, polyisoprene and styrene-butadiene rubber. In yet another modification, the ring-alkylated di(hydroxyphenyl) compound is substituted for a portion of the BPA employed in the conventional production of thermoplastic resins, e.g., arylate resins, and the resulting polymeric material will exhibit some degree of self-curing. The rigid, insoluble products obtained by heating the arylcyclobutenealkylated di(hydroxyphenyl) compounds are processed by methods conventional for thermoset-type resins. Such resins find utility in applications where conventional thermoset resins are employed, e.g., coatings and structural materials such as the aerospace and electronic industries.

The invention is further illustrated by the following Illustrative Embodiments which should not be construed as limiting the invention.

ILLUSTRATIVE EMBODIMENT I

To a solution of 18.3 g (80 mmol) of 2,2-di(4-hydroxyphenyl)-propane in 400 ml of 1,2-dichloroethane at 60° C. was added 6.1 g (40 mmol) of 4-chloromethylbenzocyclobutene and 0.4 g of zinc chloride. The resulting mixture was heated at reflux for 3 hours and then cooled to ambient temperature. The mixture was then washed with dilute hydrochloric acid and then with water, dried over magnesium sulfate and decolorized with charcoal. Removal of the diluent under reduced pressure afforded a viscous amber oil. This crude product was chromatographed through a silica gel column using chloroform as an element. The first 500 ml of eluent from the column was concentrated under reduced pressure to give 12.1 g of a glassy solid. The proton NMR spectra of the product were consistent with a mixture of benzocyclobutenemethylated 2,2-di(4-hydroxyphenyl)-propane with an average substitution of 1.1 benzocyclobutenemethyl moieties per molecule of 2,2-di(4-hydroxyphenyl)propane.

ILLUSTRATIVE EMBODIMENT II

A mixture of 0.86 g (approx. 2.5 mmol) of the product of Illustrative Embodiment I and 10.84 g (47.5 mmol) 2,2-di(4-hydroxyphenyl)-propane was added to a mixture of 4.5 g sodium hydroxide, 3.0 g lauryl sulfate, 50 ml 1,2-dichloroethane and 300 ml of water. The mixture was placed in a Waring blender and cooled to 0° C. A solution of isophthaloyl chloride (5.08 g, 25 mmol) and terephthaloyl chloride (5.08 g, 25 mmol) in 100 ml of 1,2-dichloroethane was added to the mixture in the blender at slow stirring speed. After the mixture was stirred for an additional 10 minutes at high speed it was poured into 350 ml of acetone and the precipitate was recovered by vacuum filtration. The precipitated polymer was washed with 500 ml of water in a Waring blender, filtered, washed in the funnel five times with 100 ml portions of water and dried at 50° C. in vacuo. Sixteen grams of an off-white powder were obtained. Proton nuclear magnetic resonance analysis indicated that the polymer had approximately 2.6% of the repeating units derived from the benzocyclobutenemethylated product of Illustrative Embodiment I. Compression molding of this polymeric product for 10 minutes at 250° C. yielded a crosslinked film having a glass transition temperature of 191° C. which did not dissolve in 1,2-dichlroethane.

A control sample without benzocyclobutene moieties was prepared by this same procedure by substituting the product of Illustrative Embodiment I with 2,2-di(4-hydroxyphenyl)propane. Compression molding at 250° C. for 15 minutes gave a film which was soluble in 1,2-dichloroethane and had a glass transition temperature of 178° C.

ILLUSTRATIVE EMBODIMENT III

When a sample of the benzocyclobutenemethylated 2,2-di(4-hydroxyphenyl)propane of Illustrative Embodiment I is heated in a mold at a temperature over 200° C., a rigid product will be obtained which is only moderately soluble in 1,2-dichloroethane.

What is claimed is:

1. A relatively insoluble, rigid polymer obtained by heating to a temperature up to about 300° C. a ring-arylcyclobutenealkylated di(hydroxyphenyl) compound having at least one arylcyclobutenealkyl substituent on at least one of the phenyl rings in which the alkyl moiety of each arylcyclobutenealkyl group is attached to a carbon atom of a six-membered aromatic ring.

2. The rigid polymer of claim 1 obtained by heating to a temperature of at least about 200° C. the compound of the formula

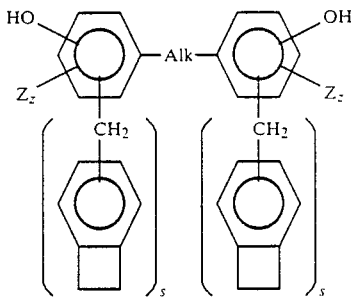

wherein Alk is alkylene of up to 8 carbon atoms inclusive, Z is alkyl or halo, z is an integer from 0 to 3 inclusive and s is an integer from 0 to 2 inclusive with the proviso that at least one s is at least 1.

3. The rigid polymer of claim 2 wherein Alk is 2,2-propylene.

4. The rigid polymer of claim 3 wherein Z is halo.

5. The rigid polymer of claim 4 wherein Z is bromo.

6. The rigid polymer of claim 5 wherein z is zero.

7. The rigid polymer of claim 6 wherein s is an integer from 0 to 1 inclusive.

8. The rigid polymer of claim 2 wherein Alk is methylene.

9. The rigid polymer of claim 8 wherein Z is halo.

10. The rigid polymer of claim 9 wherein Z is bromo.

11. The rigid polymer of claim 9 wherein z is zero.

12. The rigid polymer of claim 10 wherein s is an integer from 0 to 1 inclusive.

* * * * *